United States Patent [19]

Matravers

[11] Patent Number: 4,610,874
[45] Date of Patent: Sep. 9, 1986

[54] HAIR CONDITIONER

[75] Inventor: Peter Matravers, Los Angeles, Calif.

[73] Assignee: Neutrogena Corporation, Los Angeles, Calif.

[21] Appl. No.: 722,964

[22] Filed: Apr. 12, 1985

[51] Int. Cl.$^4$ .............................................. A61K 7/06
[52] U.S. Cl. ...................... 424/70; 514/801; 514/881
[58] Field of Search ................... 424/70; 514/863, 801, 514/881

[56] References Cited

U.S. PATENT DOCUMENTS 3,954,725  5/1976  Johnsen et al. .................. 260/123.7
4,186,188  1/1980  Gumprecht et al. ............ 260/123.7

OTHER PUBLICATIONS

McCarthy et al., Cosmetics & Toiletries, 4/1979, vol. 94, Part II, pp. 90, 92, 93.
Schoenberger et al., Cosmetics & Toiletries, 3/1979, vol. 94, pp. 57 to 60, 63, 64.
Garlen, Cosmetics & Toiletries, vol. 94, 3/1979, pp. 66 to 68.
Fleischner et al., Cosmetics & Toiletries, 3/1979, vol. 94, pp. 69 & 70.
Cannell, Cosmetics & Toiletries, 3/1979, vol. 94, pp. 29 to 31.

Primary Examiner—Dale R. Ore
Attorney, Agent, or Firm—Richard R. Mybeck

[57] ABSTRACT

A clear freely pourable base composition for hair conditioner products comprising, in weight percent, from about 0.1 to about six percent of a derivative of ethoxylated/acetylated lanolin; from about 0.1 to about 1.0 percent of an ionic polymer; from about 0.5 to about 1.0 percent hydroxyethyl cellulose; and a solvent selected from the group consisting of purified water and a water-alcohol mixture. Cationic/anionic grooming agents can be added with cellulose derivatives and viscosity modifiers.

15 Claims, No Drawings

HAIR CONDITIONER

The present invention relates to substantially homogeneous oil-free, fatty alcohol-free hair conditioner base containing as key ingredients a derivative of ethoxylated/acetylated lanolin such as ethoxylated chlosterol (C.T.F.A. name: Choleth 24) and a cationic polymer.

BACKGROUND OF INVENTION

Most conventional hair conditioners are either poorly formulated or too substantive and produce undesirable "build-up" and over conditioning after extended use. In addition, these conditioners required a very delicate and sensitive emulsification/micell formation to form a cationic conditioner base and as a result, production is both time consuming and costly.

The prior art conditioner bases, that is, those carrier compositions which accept and dispense hair conditioning reagents, usually contained stearalkonium chloride or its equivalent and such effectively precluded the use of many anionic polymers known to provide certain desirable properties such as strengthening the hair fibers and improving the hold of the hair.

A need currently exists for a new conditioner base which overcomes the arduous procedures of the prior methods, eliminates the undesirable build-up on the user's hair which characterized the prior formulations, and which provides a non-ionic surface active base which allows a broad spectrum of ingredients to be readily incorporated thereinto without compromising product stability and thereby provide hair conditioning properties heretofore unobtainable with prior art formulations.

The present invention is predicated upon fulfilling those needs with a homogeneous water-based clear non-ionic conditioner base which eliminates the oils and waxes heretofore contained in those opaque prior art conditioners which required the presence of fatty alcohols, such as cetyl and cetearyl, and stearalkonium chloride and which accomplishes conditioning in a safe and effective manner.

SUMMARY OF INVENTION

The present invention is directed to a novel homogeneous water-based, clear, freely pourable, cationic hair conditioner base which is free of both oil and fatty alcohols and when formulated, as hereinafter described, into a finished conditioner, provides a product which materially reduces residual deposits on the hair even after extensive use. More particularly the present invention provides a new and improved hair conditioner formulation having enhanced conditioning and aesthetic qualities which contains a derivative of an ethoxylated/acetylated lanolin such as ethoxylated chlosterol ("Choleth 24") and a cationic polymer. In addition to improving both the appearance and the managability of the human hair with which it is used, the new conditioner base has the surprising propensity of permitting therapeutic agents such as coal tar extract and the like to be readily blended thereinto with minimal difficulty and provides improved aesthetic qualities with little or no undesirable side effects.

The salient feature of this invention is the unique combination of the derivatives of ethoxylated-/acetylated lanolin with cationic polymers which allows other lanolin derivatives, hydrolyzed animal protein, and the like to be readily blended thereinto without adversely affecting either the clarity or the mildness thereof. These and other additives may be readily employed to add body, shine and manageability to the hair without creating the reagent buildup and its accompanying dinginess which characterized prior art formulations.

Accordingly, a principle object of the present invention is to provide a new and improved hair conditioner which is both oil and fatty alcohol free.

Another object of the present invention is to provide a new and improved hair conditioner which avoids the undesirable buildup characterizing repeated use of currently available substantive conditioners.

A further object of the present invention is to provide an oil free, fatty alcohol free hair conditioner which provides both body and lubricity for easy combing and which allows the incorporation of a variety of anionic or cationic ingredients without detracting therefrom.

Still another object of the present invention is to provide an improved conditioner base which is water soluble and readily delivers conditioner reagents to the hair to provide the benefits thereof without incurring either eye irritation or the deleterious side and after effects which characterizes those conditioners using oils, fatty alcohols, and stearalkonium chloride as delivery media.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

In one practice of the present invention, a composition is formulated by introducing into a batch blender while providing continuous agitation an amount of hydroxyethylcellulose, Quaternium 19 (CTFA name; available as Polymer JR from Union Carbide) and purified water and heating the mixture to about 75° C. Thereafter, an amount of Choleth-24 (CTFA name; available as Solulan ® C-24 from Amerchol) is added while maintaining both the stirring and the temperature. When a homogeneous mixture is obtained, any of a variety of known conditioning agents can be blended into the mixture to achieve the end properties desired for the ultimate commercial formulation. Included among the additives found acceptable are polyvinyl pyrrolidone ("PVP") for body and hold; Laneth-16 for sheen; propylene glycol for shine and the like. Other cationic conditioning agents which are compatible with the conditioner base hereof are Quaternium-23 (Gafquat 755N), Quaternium-26 (Ceraphyl 65), Quaternium-39 (Reten), Quaternium-41 (Merquat), Olealkonium Chloride (Alacsan 7 LUF), Cetrimonium Chloride (Barquat CT), and the like. Non-ionic moisturizing ingredients useful herein include sodium PCA (Ajidew $N_{50}$), glycerine (Glycerol), soluble collagen (Collasol), hydrolyzed animal protein (Lexein; Peptein), panthenol, quaternized hydrolysate of collagen and the like. After the desired conditioning ingredients and appropriate preservatives are blended into the batch, the batch is cooled to ambient temperature and fragrance is added. Thereafter the formulation is ready for packaging.

A representative formulation embodying the present invention will contain in percent by weight from about 0.1 to about 0.8 percent hydroxyethylcellulose (Natrosol ®, Hercules); about 0.2 to about 0.8 percent PVP; about 1 to about 4 percent Solulan C-24; about 0.1 to about 2 percent Solulan 16; about 0.4 to about 0.8 percent Quaternium-19 (Polymer JR, Union Carbide); about 1 to about 4 percent Cocamidopropyldimonium Hydroxypropylamino Collagen (Lexein QX 3000, Inolex); from about 0.1 to about 0.15 percent methylparaben, 0.05 percent propylparaben, about 0.1 to about 0.3 percent imidazolidinyl urea (Germall 115, Sutton); about 2 to about 8 percent propylene glycol; about 0.2 to about 0.3 percent fragrance; and qs purified water.

If desired, the above formulation can be modified to include from about 1 to about 2 percent coal tar extact dissolved in about 10 to about 15 percent anhydrous ethyl alcohol. Further, viscosity modifiers such as synthetic gum, gar gum and the like have been found both compatible and useful herewith.

As will appear, the conditioner base of this invention, because of its surface active base enjoys the versatility of permitting many cationic and anionic ingredients to be added thereto without upsetting either the stability or the balance of the base.

Other recognized reagents for hair care products which can be employed herein and the function they fulfill are: vinylpyrrolidone/vinyl acetate copolymers (PVP/VA) which are film formers, hair thickeners, and promote hair styling; agents AT845, AT937 and AT958 (also known as copolymers 845, 937 and 958, respectively) which impart a pleasant "feel", enhance hold and curl retention; silicone glycol polymers (available as Dow fluids 190 and 193), ethylene oxide polymers (available as Polyox), and Guar hydroxypropyltrimonium chloride (available as Jaguar C-17), all of which are detangling agents; keratin amino acids (also known as Croteins) which improve hair strength and manageability; Quaternium 22 (available as "Ceraphyl 60") and Quaternium 40 (available as "Merquat 100") which enhance manageability and prevents flyaway; and sodium isostearoyl-2-lactylate (available as "Pationic ISL") which provides improved feel and moisturizes.

To further aid in the understanding of the present invention, and not by way of limitation, the following examples are presented.

EXAMPLE I

With continuous mixing, hydroxyethylcellulose and Quaternium-19 are dispensed in purified water and heated to 75° C. While maintaining the temperature at 75° C., Soluban C-24 is blended into the water-cellulose mixture to form a homogeneous blend. The type and level of specific conditioning agents are then selected and blended into the blend, e.g., Quaternium 23 (now named polyquaternium 11), glycerin, PVP and the like, and the batch is cooled to ambient temperature. Thereafter the desired amounts of fragrance and anhydrous ethyl alcohol (e.g., SD 40), if any, are added and the formulation, shown below by weight percent, is ready for packaging. The formula was clear, freely pourable and free of both oil and fatty alcohol.

| Purified Water | 84.32% |
|---|---|
| Natrosol | .85% |
| Polymer Jr. (30 M) | .8% |
| Solulan C-24 | 2.0% |
| PVP (k30) | .5% |
| Citric acid 50% | .03% |
| Methylparaben | .15% |
| Propylparaben | .05% |
| Germall 115 | .3% |
| Propylene glycol | 5.0% |
| Quaternium-23 | 2.0% |
| Sodium PCA | 3.0% |
| Glycerin | 1.0% |

EXAMPLE II

Following the procedure of Example I, a clear, freely pourable, oil-free, fatty alcohol-free hair conditioner was prepared having the following formulation in percent by weight.

| Purified Water | 73.37% |
|---|---|
| Natrosol | .7% |
| Polymer Jr. (30 M) | .6% |
| Solulan C-24 | 2.0% |
| PVP (k30) | .3% |
| Citric acid 50% | .03% |
| Methylparaben | .15% |
| Propylparaben | .05% |
| Germall 115 | .3% |
| Propylene glycol | 8.0% |
| Fragrance | .5% |
| Coal tar extract | 2.0% |
| SD 40 Alcohol | 12.0% |

EXAMPLE III

Following the procedure of Example I, a clear, freely pourable, oil-free, fatty alcohol-free hair conditioner was prepared having the following formulation in percent by weight.

| Purified Water | 78.27% |
|---|---|
| Natrosol | .8% |
| Polymer Jr. (30 M) | .6% |
| Solulan C-24 | 2.0% |
| PVP (k30) | .3% |
| Citric acid 50% | .03% |
| Methylparaben | .15% |
| Propylparaben | .05% |
| Germall 115 | .3% |
| Propylene glycol | 4.0% |
| Fragrance | .5% |
| Coal tar extract | 1.0% |
| SD 40 Alcohol | 12.0% |

EXAMPLE IV

A conditioner prepared according to the procedure of Example I having a composition, in weight percent, of:

| Purified Water | 70.77% |
|---|---|
| Natrosol | .4% |
| Polymer Jr. (30 M) | .8% |
| Solulan C-24 | 2.0% |
| PVP (k30) | .5% |
| Citric acid 50% | .03% |
| Methylparaben | .15% |
| Propylparaben | .05% |
| Germall 115 | .3% |
| Propylene glycol | 8.0% |
| Coal tar extract | 2.0% |
| SD 40 Alcohol | 15.0% | was compared with a commercial product (AGREE ®, regular conditioner) in a modified Draize Eye Irritation study. The Modified Draize Eye Test (See: 16 CFR 1500.42 and "Recommended Guidelines for Accute Eye Irritation Testing", Interagency Regulatory Liason Group 1981). The tests, performed in accordance with the cited references, involved nine (9) New Zealand albino rabbits whose eyes were adjudged free from occular defects. The test material was instilled into the conjunctival sac of each of six (6) animals, the lids held together for one (1) second, after which the rabbits were returned to their cages. The remaining three animals were tested in the same manner except that the test material was flushed from the eye with 140 ml of water after an exposure period of five (5) seconds. The untreated eye in each rabbit served as a control. Ocular irritation was evaluated at twenty-four (24), forty-eight (48), seventy-two (72) hours and, if any occular irritation was present at 72 hours, at seven (7) days in accordance with the grading scale shown below.

IRRITATION RATING

| RATING | RANGE OF MEAN SCORE | DEFINITION |
|---|---|---|
| Non-Irritating | 0.0–0.5 | To maintain this rating, all scores at the 48-hour reading must be zero; otherwise increase rating one level. |
| Practically Non-Irritating | Greater than 0.5–2.5 | To maintain this rating, all scores at the 48-hour reading must be zero; otherwise increase rating one level. |
| Minimally Irritating | Greater than 2.5–15.0 | To maintain this rating, all scores at the 72-hour reading must be zero; otherwise increase rating one level. |
| Mildly Irritating | Greater than 15.0–25.0 | To maintain this rating, all scores at the 7-day reading must be zero; otherwise increase rating one level. |
| Moderately irritating | Greater than 25.0–50.0 | To maintain this rating, scores at 7 days must be less than or equal to 10 for 60% or more of the animals. Also mean 7-day score must be less than or equal to 20 and more than 60% of animals show scores less than 10, then no animal among those showing scores greater than 10 can exceed a score of 30 if rating is to be maintained; otherwise, increase rating one level. |
| Severely Irritating | Greater than 50.0–80.0 | To maintain this rating, scores at 7 days must be less than or equal to 30 for 60% or more of the animals. Also mean 7-day score must be less than or eual to 40. If 7-day mean score is less than or equal to 40 and more than 60% of the animals show scores less than 10 or equal to 30, then no animal among those showing scores greater than 30 can exceed a score of 60 if rating is to be maintained; otherwise, increase rating one level. |
| Extremely Irritating | Greater than 80.0–110.0 | |

The samples were tested undiluted with 0.1 ml instilled into each eye tested. The results obtained are reported in Table A.

TABLE A

| Time Hour/day | TEST SAMPLE Unwashed Eyes | TEST SAMPLE Washed Eyes | AGREE ® CONDITIONER Unwashed Eyes | AGREE ® CONDITIONER Washed Eyes |
|---|---|---|---|---|
| 24 hrs | 5.33 | 0 | 8.66 | 3.64 |
| 48 hrs | 2.64 | 0 | 4.33 | 1.34 |
| 72 hrs | 0 | 0 | 2.64 | 0 |
| 7 days | 0 | 0 | 1.00 | 0 |
| Rating: | Minimally Irritating | Non-irritating | Moderately Irritating | Minimally Irritating |

EXAMPLE V

Additional testing was conducted to compare the tar conditioner described in Example IV with a commercially available product (AGREE ® conditioner). Protocol denominated "Modified CFR Occular Instillation Test", "CFR Primary Skin Irritation Test" and "Acute Oral Toxicity Test" were employed. Both products passed the primary skin irritation and acute oral toxicity test with little difference in results. In the Modified CFR Ocular Irritation Test, nine healthy New Zealand white rabbits were used. Both eyes were examined at 0 hour and each was assigned a score. 0.2 milliliters of the substance to be tested was instilled into the right eye of each of the nine rabbits. The left eye was untreated and served as the control. For three of the rabbits in each set, the eye was rinsed with normal saline immediately following the administration of the tested substance. Thereafter, both eyes were examined at 24, 48 and 72 hours post-instillation. As shown below, the tar conditioner embodying the present invention was notably safer and milder (slight redness in only one of nine test animals) than was the commercial product (caused redness and chemosis in five of nine test animals).

TABLE B

| Rabbit | | Observations (hours post-instillation) | | | |
|---|---|---|---|---|---|
| | | 0 | 24 | 48 | 72 |
| Tested substance: Example IV | | | | | |
| 101 | Test | 0 | A | 0 | A |
| | Control | 0 | 0 | 0 | 0 |
| 102 | Test | 0 | 0 | 0 | 0 |
| | Control | 0 | 0 | 0 | 0 |
| 103 | Test | 0 | 0 | 0 | 0 |
| | Control | 0 | 0 | 0 | 0 |
| 104 | Test | 0 | 0 | 0 | 0 |
| | Control | 0 | 0 | 0 | 0 |
| 105 | Test | 0 | 0 | 0 | 0 |
| | Control | 0 | 0 | 0 | 0 |
| 106 | Test | 0 | 0 | 0 | 0 |
| | Control | 0 | 0 | 0 | 0 |
| 107 R | Test | 0 | 0 | 0 | 0 |
| | Control | 0 | 0 | 0 | 0 |
| 108 R | Test | 0 | 0 | 0 | 0 |
| | Control | 0 | 0 | 0 | 0 |
| 109 R | Test | 0 | 0 | 0 | 0 |
| | Control | 0 | 0 | 0 | 0 |
| Tested substance: AGREE ® | | | | | |
| 201 | Test | 0 | A,B | A | 0 |
| | Control | 0 | 0 | 0 | 0 |
| 202 | Test | 0 | A | A | A |
| | Control | 0 | 0 | 0 | 0 |
| 203 | Test | 0 | A* | A | A |
| | Control | 0 | 0 | 0 | 0 |
| 204 | Test | 0 | 0 | 0 | 0 |
| | Control | 0 | 0 | 0 | 0 |
| 205 | Test | 0 | A | A | 0 |
| | Control | 0 | 0 | 0 | 0 |
| 206 | Test | 0 | A* | A | 0 |
| | Control | 0 | 0 | 0 | 0 |
| 207 R | Test | 0 | 0 | 0 | 0 |

TABLE B-continued

| Rabbit | | Observations (hours post-instillation) | | | |
|---|---|---|---|---|---|
| | | 0 | 24 | 48 | 72 |
| 208 R | Control | 0 | 0 | 0 | 0 |
| | Test | 0 | 0 | 0 | 0 |
| | Control | 0 | 0 | 0 | 0 |
| 209 R | Test | 0 | 0 | 0 | 0 |
| | Control | 0 | 0 | 0 | 0 |

Code:
0 = No reaction
A = (IIIA1) = Conjunctivae, Redness, Some vessels definitely injected
R = Rinsed
B = (IIIB1) Chemosis, above normal swelling (includes nictitating membranes)
*slight mucous discharge

EXAMPLE VI

A tar conditioner was prepared in accordance with the procedure of Example IV having a composition, in weight percent of:

| | |
|---|---|
| Purified Water | 72.8% |
| Natrosol | .6% |
| Polymer Jr. (30 M) | .5% |
| Solulan C-24 | 2.0% |
| PVP (k30) | .4% |
| Solulan 16 | .4% |
| Methylparaben | .15% |
| Propylparaben | .05% |
| Germall 115 | .3% |
| Propylene glycol | 6.0% |
| Fragrance | .3% |
| Coal tar extract | 1.5% |
| SD 40 Alcohol | 15.0% |

Like amounts of commercially available conditioners were obtained and all test samples were spiked with fluorescein, a special fluorescent dye. Swatches were prepared with virgin hair and damaged hair (i.e., perm treated). The conditioner was applied to the several hair swatches and after the proscribed time, rinsed therefrom. Measurements were than taken to determine the residue (in percent) remaining on the hair after the prewash (rinse). The results using ten swatches and taking the average of three trials are reported in Table C.

TABLE C

| Specimen | Residue (Average % remaining) | |
|---|---|---|
| | Virgin Hair | Damaged Hair |
| FLEX ® (Revlon) | 0.668± | 1.209 |
| SILKIENCE ® (Gillette) | 1.511± | 1.652 |
| SILKIENCE ® (Gillette) | 2.375± | 2.384 |
| CLAIROL ® (Clairol, Inc.) | 0.635± | 0.907 |
| CLAIROL ® EXTRA (Clairol, Inc) | 1.090± | 1.294 |
| AGREE ® (Johnson and Son) | 0.547± | 0.972 |
| AGREE ®EXTRA (Johnson and Son) | 0.634± | 1.268 |
| L'OREAL ® Protein (Cosmoir, Inc.) | 0.796± | 1.103 |
| L'OREAL ® Regular (Cosmoir, Inc.) | 0.640± | 0.842 |
| IVORY ® (Proctor & Gamble) | 1.223± | 1.601 |
| FINESSE ® (Helene Curtiss) | 0.896± | 1.347 |

TABLE C-continued

| Specimen | Residue (Average % remaining) | |
|---|---|---|
| | Virgin Hair | Damaged Hair |
| EXAMPLE VI | 0.462± | 0.562 |

From the foregoing, it is apparent that the material of Example VI produced a highly satisfactory level of conditioning residue after rinse (Prewash residue).

EXAMPLE VII

The samples of Example VI were further tested to determine the ability for the conditioners to be removed by shampooing (Wash 1, Wash 2, etc.) as a measure of "conditioner build-up". The results are reported in Table D-1 and D-2.

TABLE D-1

| Specimen | Residue (Average % remaining) | | | |
|---|---|---|---|---|
| | Wash 1 | Wash 2 | Wash 3 | Wash 4 |
| Virgin Hair | | | | |
| FLEX ® | .237 | .071 | | |
| SILKIENCE ® EXTRA | .620 | .345 | .121 | .030 |
| SILKIENCE ® | .358 | .141 | .047 | |
| CLAIROL ® | .225 | .106 | | |
| CLAIROL ® EXTRA | .699 | .435 | .111 | |
| AGREE ® | .174 | .079 | | |
| AGREE ® EXTRA | .241 | .132 | .041 | |
| L'OREAL ® Protein | .424 | .189 | .077 | |
| L'OREAL ® Regular | .234 | .097 | | |
| IVORY ® | .844 | .485 | .301 | .141 |
| FINESSE ® | .407 | .223 | .068 | |
| EXAMPLE VI | .028 | | | |
| Damaged Hair | | | | |
| FLEX ® | .812 | .406 | .244 | .087 |
| SILKIENCE ® EXTRA | 1.811 | 1.355 | .824 | .389 |
| SILKIENCE ® | 1.031 | .675 | .315 | .094 |
| CLAIROL ® | .516 | .210 | .067 | |
| CLAIROL ® EXTRA | 1.294 | .722 | .419 | .211 |
| AGREE ® | .618 | .324 | .122 | |
| AGREE ® EXTRA | .785 | .361 | .161 | |
| L'OREAL ® Protein | .665 | .307 | .140 | |
| L'OREAL ® Regular | .504 | .262 | .034 | |
| IVORY ® | .894 | .363 | .245 | .080 |
| FINESSE ® | .772 | .310 | .167 | |
| EXAMPLE VI | .183 | .072 | | |

In each test the conditioner produced according to the present invention (Example VI) was readily and completely removed with only one or two washings thereby preventing conditioner buildup.

EXAMPLE VIII

A sample prepared pursuant to Example VI was traced through a sequence of seven conditioning and shampoo cycles and the residues measured using the florescein previously described. Similar data was accumulated for AGREE ®, FINESSE ®, CLAIROL ®, CLAIROL ® EXTRA, and SILKIENCE ® EXTRA. The results which unequivocally demonstrated a signficantly reduced buildup of residues after extended use are reported in Table E.

TABLE E

| Specimen | Residue remaining after conditioning/shampoo cycle | | | | | | |
|---|---|---|---|---|---|---|---|
| | Cycle 1 | Cycle 2 | Cycle 3 | Cycle 4 | Cycle 5 | Cycle 6 | Cycle 7 |
| SILKIENCE ® EXTRA | 2.342 | 2.971 | 3.582 | 3.976 | 4.068 | 4.040 | 4.102 |
| CLAIROL ® | .644 | .806 | .911 | 1.052 | 1.033 | 1.045 | 1.037 |
| CLAIROL ® EXTRA | 1.203 | 1.788 | 1.917 | 2.018 | 2.137 | 2.244 | 2.303 |
| AGREE ® | .212 | .309 | .468 | .622 | .814 | .944 | .930 |

TABLE E-continued

| Specimen | Residue remaining after conditioning/shampoo cycle | | | | | | |
|---|---|---|---|---|---|---|---|
| | Cycle 1 | Cycle 2 | Cycle 3 | Cycle 4 | Cycle 5 | Cycle 6 | Cycle 7 |
| FINESSE ® | .855 | 1.134 | 1.267 | 1.434 | 1.469 | 1.411 | 1.404 |
| EXAMPLE VI | .096 | .146 | .217 | .203 | .222 | .216 | .236 |

The adopted names used herein are published in the "CTFA Cosmetic Ingredient Dictionary" 2nd edition, published by The Cosmetic, Toiletry and Fragrance Association, Inc., 1110 Vermont Avenue, N.W., Washington, D.C. 20005. The terms reported therein are well known to those skilled in the art to which the present invention pertains. "Solulan C-24" (also known as "Choleth-24") is the polyethylene glycol ether of chlosterol (q.v.) with an average ethoxylation value of 24.

"Solulan 16" (also known as "Laneth-16") is the polyethylene glycol ether of lanolin alcohol (q.v.) with an average ethoxylation value of 16.

"Quaternium 19" (officially changed to "Polyquaternium-10" in CTFA Cosmetic Ingredient Dictionary, 3rd Edition) is a polymeric quaternary ammonium salt of hydroxyethyl cellulose reacted with a trimethyl ammonium substituted epoxide.

"Quaternium 23" (officially changed to "Polyquaternium 11" in the CTFA Dictionary, 3rd Edition) is a quaternary ammonium polymer formed by the reaction of dimethyl sulfate and a copolymer of vinyl pyrrolidone and dimethylaminoethyl methacrylate.

Each of the other ingredients defined herein by its CTFA adopted name are intended to conform to the substance set forth under that specific name in the CTFA Cosmetic Ingredient Dictionary, which definitions are incorporated herein by this reference thereto.

It is understood that such modifications, alterations and adaptations, as may readily occur to the artisan skilled in the field to which this invention pertains when confronted with this specification, are intended within the spirit of the present invention which is limited only by the scope of the claims appended hereto.

What is claimed is:

1. A clear wax-free oil-free pourable water soluble base for formulating hair care products consisting in weight percent of: from about 0.1 to about 6 percent ethoxylated cholesterol; from about 0.1 to about 1.0 percent of a polymeric quaternary ammonium salt of hydroxyethyl cellulose reacted with a trimethyl ammonium substituted epoxide; from about 0.5 to about 1.0 percent hydroxyethyl cellulose; and at least 90 percent of a solvent selected from the group consisting of purified water and a water-alcohol mixture.

2. A base composition according to claim 1 containing viscosity modifier.

3. A base composition according to claim 2 in which said viscosity modifier consists of from about 0.5 to about 0.8 percent synthetic gum.

4. A hair care product for conditioning hair comprising the base composition of claim 1 and one or more grooming agents which add body, shine and manageability to the hair.

5. A hair care product according to claim 4 in which said grooming agents are selected from the group consisting of polymers and copolymers of vinyl pyrrolidone and vinyl ether.

6. A hair care product according to claim 4 in which said grooming agent is a quaternized hydrolysate of collagen.

7. A hair care product according to claim 4 containing a viscosity modifier.

8. A hair care product according to claim 7 in which said viscosity modifier comprises from about 0.5 to about 0.8 percent synthetic gum.

9. A base composition according to claim 1 containing from about 2 to about 8 percent by weight of propylene glycol.

10. A hair care product for conditioning hair comprising the base composition of claim 9 and one or more grooming agents which add body, shine and manageability to the hair.

11. A hair care product according to claim 10 in which said grooming agents are selected from the group consisting of polymers and copolymers of vinyl pyrrolidone and vinyl ether.

12. A hair care product according to claim 10 in which said grooming agent is a quaternized hydrolysate of collagen.

13. A base composition according to claim 9 containing a viscosity modifier.

14. A base composition according to claim 13 in which said viscosity modifier comprises from about 0.5 to about 0.8 percent synthetic gum.

15. A hair care product for conditioning hair comprising, in percent by weight, from about 0.1 to about 0.8 percent hydroxyethylcellulose; from about 0.2 to about 0.8 percent polyvinyl pyrrolidine; about 0.1 to about 4 percent of the polyethylene glycol ether of cholesterol (q.v.) with an average ethoxylation value of 24 ("Choleth 24"); about 0.1 to about 2 percent of the polyethane glycol ether of lanolin alcohol (q.v.) with an average ethoxylation value of 16 ("Laneth 16"); about 0.4 to about 0.6 percent the polymeric quaternary ammonium salt of hydroxyethyl cellulose reacted with a trimethyl ammonium substituted epoxide ("Polyquaternium-10"); about 1 to about 4 percent cocamidopropyl-dimonium hydroxypropylamino collagen; from about 0.1 to about 0.15 percent methylparaben; about 0.05 percent propylparaben; about 0.1 to about 0.3 percent imidazolidinyl urea; about 2 to about 8 percent propylene glycol; about 0.2 to about 0.3 percent fragrance; and q.s. purified water.

* * * * *